United States Patent [19]
Adams

[11] Patent Number: 6,019,504
[45] Date of Patent: *Feb. 1, 2000

[54] METHOD OF AND AN APPARATUS FOR PHOTOTHERMALLY EXAMINING WORKPIECE SURFACES

[75] Inventor: Horst Adams, Nonnenhorn, Germany

[73] Assignee: Wagner International AG, Altstatten, Switzerland

[ * ] Notice: This patent issued on a continued prosecution application filed under 37 CFR 1.53(d), and is subject to the twenty year patent term provisions of 35 U.S.C. 154(a)(2).

[21] Appl. No.: 08/865,384

[22] Filed: May 29, 1997

[30] Foreign Application Priority Data

Jun. 10, 1996 [DE] Germany .............................. 196 23 121

[51] Int. Cl.⁷ .................................................. G01N 25/72
[52] U.S. Cl. .................................................................. 374/5
[58] Field of Search ................... 374/5, 126; 250/339.05, 250/339.01, 341.1, 341.8, 548, 559.01, 559.03, 559.04, 559.27, 359.1, 360.1

[56] References Cited

U.S. PATENT DOCUMENTS

| | | | |
|---|---|---|---|
| 4,551,030 | 11/1985 | Luukkala et al. | 374/5 |
| 4,757,200 | 7/1988 | Sheperd | 250/347 |
| 4,785,185 | 11/1988 | Izatt et al. | 250/339 |
| 4,810,088 | 3/1989 | Karning et al. | 250/347 |
| 5,094,544 | 3/1992 | Ignatowicz | 374/126 |
| 5,343,043 | 8/1994 | Johnson | 250/339.01 |
| 5,410,154 | 4/1995 | Broicher et al. | 250/339.05 |

FOREIGN PATENT DOCUMENTS

| | | | |
|---|---|---|---|
| 30 37 983 C2 | 4/1982 | Germany | G01N 21/00 |
| 38 20 862 A1 | 12/1989 | Germany | G01N 21/62 |
| 0 609 193 A2 | 8/1994 | Germany | G01B 15/02 |
| 43 43 076 A1 | 6/1995 | Germany | G01N 21/84 |

*Primary Examiner*—William Oen
*Attorney, Agent, or Firm*—Fenwick & West, LLP

[57] ABSTRACT

A method of photothermally examining workpiece surfaces, wherein an electromagnetic exciting beam is directed from a measuring unit to a point to be measured on the workpiece surface so as to heat the workpiece surface at that point and, furthermore, the heat radiation emitted from the point to be measured is detected and analyzed, is characterized in that a plurality of selected points to be measured on the workpiece surface are irradiated by at least a partial beam of the exciting beam, and the heat rays issuing from the points to be measured are sensed and subjected to joint analysis.

17 Claims, 3 Drawing Sheets

METHOD OF AND AN APPARATUS FOR PHOTOTHERMALLY EXAMINING WORKPIECE SURFACES

FIELD OF THE INVENTION

The instant invention relates to a method of photothermally examining workpiece surfaces, as recited in the preamble of claim 1.

BACKGROUND OF THE INVENTION

A method of the kind in question is known, for instance, from DE-A-38 20 862. During recent years photothermal examination of the surface of workpieces has proved to be a successful method of investigating workpiece surfaces in a contact-free and non-destructive manner. With this method, excitation radiation modulated in intensity, especially laser radiation is applied to heat the surface of a workpiece at a point to be measured, and the heat radiated from the point to be measured is detected and analyzed.

It is known from EP-A-0 609 193 to direct a continuous or a modulated laser beam, modulated with mechanical interruption, against a surface to be examined. On that surface, the laser beam generates periodic heating which is detected by an infrared sensor, then converted, and applied to a computer for evaluation.

In the case of another known apparatus for photothermal examination the laser excitation beam and the thermal beam it generates at the point to be measured are collinear (see DE 43 43 076 A1).

Publication DE-A-38 20 862 discloses a measuring system provided with an aperture diaphragm to subdivide a pulsating laser beam into a plurality of partial beams which are directed simultaneously to a body to be examined. The heat radiation emitted by the body under examination is sensed by a thermo-image camera.

An apparatus for optical examination of workpiece surfaces, comprising a detector diode array on which illuminated points of a sample are imaged is known from DE-A-30 37 983.

SUMMARY OF THE INVENTION

It is an object of the invention to provide a method and an apparatus which permit measurements to be taken at a plurality of selected points, using only one excitation source.

The object is met by a method as defined in claim 1 and by an apparatus as defined in claim 5.

A method according to the invention and an apparatus according to the invention both are characterized in that a plurality of points selected for measurement and disposed, for example, in a grid pattern on the surface of a workpiece can be handled by a single excitation source, especially a laser, such as a $CO_2$ laser. That can be accomplished either simultaneously or successively, depending on the particular embodiment. In the case of simultaneous operation, the exciting beam is split into partial beams of equal intensity directed to a plurality of points to be measured at the same time.

In its most general embodiment, the apparatus according to the invention comprises optical means for directing at least a partial beam of the exciting beam to a plurality of points selected for measurement on the surface of a workpiece. The detector means in that case is embodied by a multiple detecting device designed to sense the heat radiation emitted by all the points being measured. A preferred modification of the invention has the optical means and the multiple detecting device integrated in the measuring unit.

Claim 7 presents a first modification of the optical means which comprises a plurality of partly reflecting mirrors disposed one behind the other in the beam path of the exciting beam. The multiple detecting device may include a plurality of detectors, each being associated with a respective one of the partly reflecting mirrors.

Alternatively, the multiple detecting device may be a heat-sensitive detector array designed in linear or matrix configuration.

Implementation of the detector array in the form of a matrix is preferred when the optical means is embodied by a mirror which is pivotable about two axes in accordance with another advantageous embodiment of the invention.

The method and apparatus according to the invention are used with particular advantage to measure the thickness of a coating film or layer on a workpiece, especially a powder coat not baked or annealed.

BRIEF DESCRIPTION OF THE DRAWING

The invention will be described further, by way of example, with reference to the accompanying drawings, in which.

DESCRIPTION OF THE PREFERRED EMBODIMENTS

Figure 1:
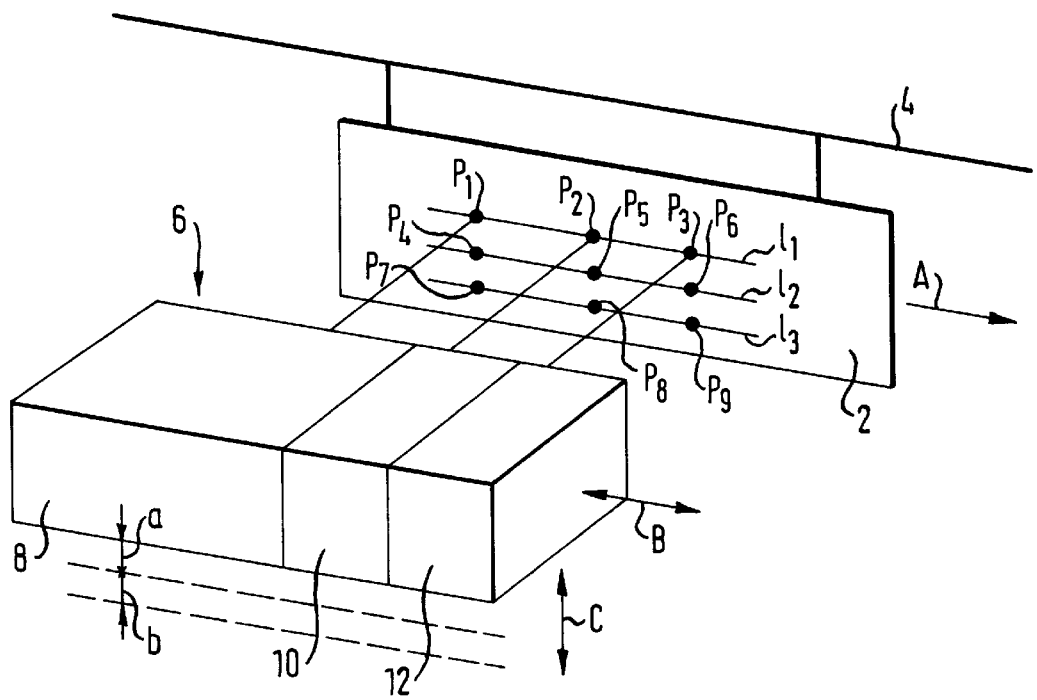
FIG. 1 is a perspective view of a first embodiment of the invention.
Figure 2:
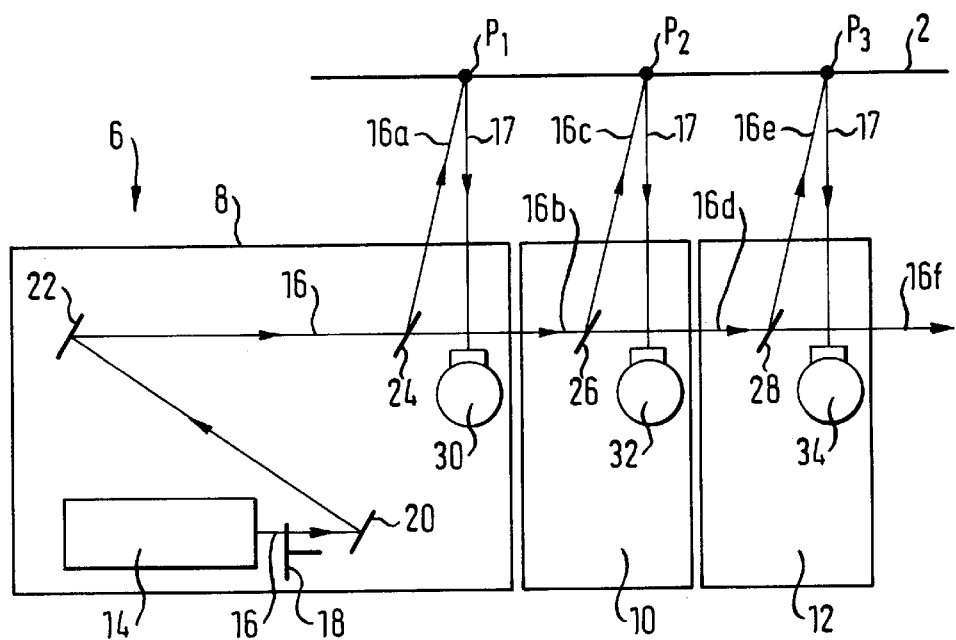
FIG. 2 is a diagrammatic top plan view of the embodiment illustrated in FIG. 1, including additional schematic presentations of aggregates not shown in FIG. 1.

A first embodiment of the invention will be described with reference to FIGS. 1 and 2.

Reference numeral 2 designates a workpiece which is being moved continuously along a conveying path 4 in the direction of arrow A. The workpiece is coated at least on the surface facing the onlooker of the drawing with a pigment powder not yet baked or annealed.

Reference numeral 6 designates a measuring unit composed of a basic or principal unit 8 and two subunits 10, 12. In general, the measuring unit 6 is movable in the direction of double arrow B, in other words parallel to and in synchronism with the workpiece as well as opposite to the same. The principal unit 8 houses a laser 14 from which issues an exciting beam 16. The exciting beam 16 is modulated by conventional modulating means, such as a chopper 18, i.e. it is interrupted periodically and deflected by mirrors 20, 22. A partly reflecting mirror 24 is disposed in the beam path of the deflected beam 16. The principal unit 8 further houses a heat-sensitive detector, briefly an IR (infrared) detector 30.

One partial beam 16a of the exciting beam is reflected by the partly reflecting mirror 24, while another partial beam 16b passes the partly reflecting mirror 24, in continuation of the exciting beam 16. This partial beam 16b impinges on another partly reflecting mirror 26 where, once more, it is split into a partial beam 16c which is reflected and a partial beam 16d which is transmitted. If desired, the transmitted partial beam 16d, too, is divided into a reflected partial beam 16e and a transmitted partial beam 16f, provided there are further subunits like the subunits 10, 12. Otherwise, the partial beam 16c is totally reflected by the partly reflecting mirror 28.

The dividing ratio of the partial beams in case of full reflection of partial beam 16d is 1:3 at the partly reflecting mirror 24, 1:1 at the partly reflecting mirror 26, and 1:0 at the partly reflecting mirror 28. Generally, the dividing ratio should be selected such that partial beams 16a, 16c, and 16e have the same radiation intensity. The dividing ratio is to be scaled accordingly if there is a different number of subunits (more than two).

The partial beams 16a, 16c, and 16e hit selected points to be measured $P_1$, $P_2$, $P_3$ which lie along a line $l_1$ on the workpiece surface. The principal unit 8 is furnished with an IR detector 30 to receive a heat ray 17 which is emitted, in a direction perpendicular to the workpiece 2, by point $P_1$ being measured.

The subunits 10, 12 likewise are equipped with IR detectors 32, 34 each receiving heat rays 17 which issue a right angles from points $P_2$, $P_3$ being measured.

In operation, during a first step the measuring unit 6, composed of the principal unit 8 and the subunits 10, 12, is moved in synchronism with the workpiece 2 and parallel to the same so that no relative movement will take place between the workpiece 2 and the measuring unit 6. Partial exciting beams 16a, 16c, 16e obtained from the single exciting beam 16 are directed simultaneously at the selected points to be measured $P_1$, $P_2$, $P_3$ located along a line $l_1$ which need not necessarily be straight. That causes heating at the selected points to be measured. The thermal radiation generated by the heating is reflected back to the measuring unit 6 from the points being measured $P_1$, $P_2$, $P_3$, with the greatest intensity at right angles. In the measuring unit, the heat radiation is picked up by the various detectors 30, 32, 34 and subjected to per se known analytical evaluation, such as conversion and subsequent processing into signals indicative of the layer thickness. This kind of converting and evaluating operation is known per se.

In a second step, while being moved on at the same speed as the workpiece 2, the measuring unit 6 is displaced by a vertical distance a. This vertical distance a corresponds to a spacing between the first line $l_1$ and a second line $l_2$ on which points to be measured $P_4$, $P_5$, and $P_6$ are located. Here, the procedures of irradiation and detection are repeated, as described above. Finally, in a third step, once again the measuring unit 6 is displaced by a distance b which may be the same in extent as the distance a and then the operations described are repeated once more for points to be measured $P_7$ $P_8$, $P_9$ located along a line $l_3$.

In this manner, using but one laser 14, a single operating cycle is sufficient to measure a plurality of points, in the given example this being the points to be measured $P_1$ to $P_9$ which are situated in a grid.

Figure 3:
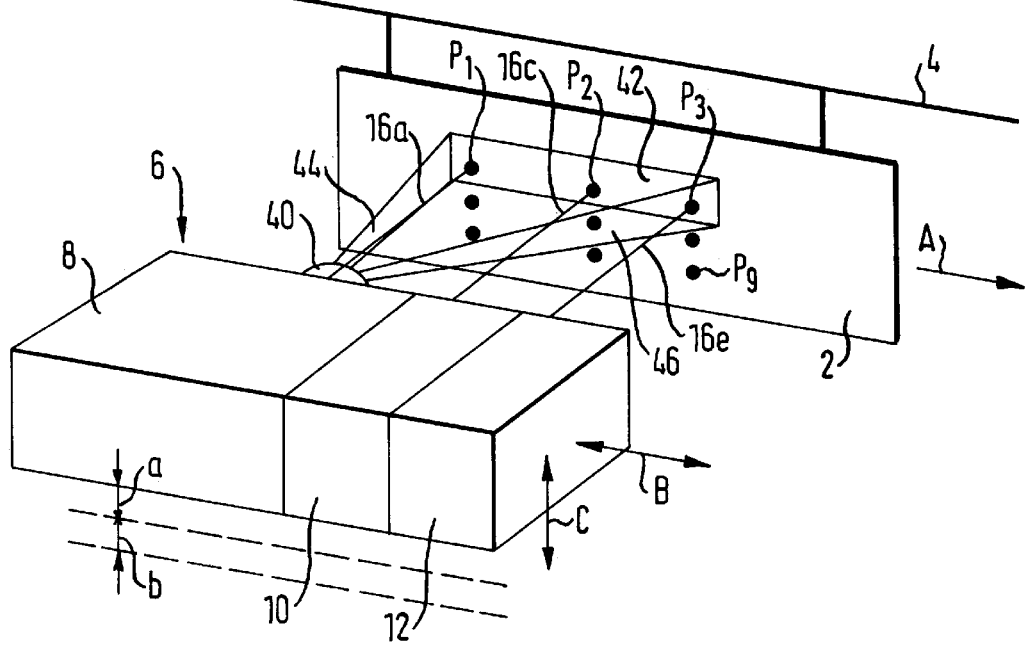
FIG. 3 is a perspective view of a second embodiment of the invention.
Figure 4:
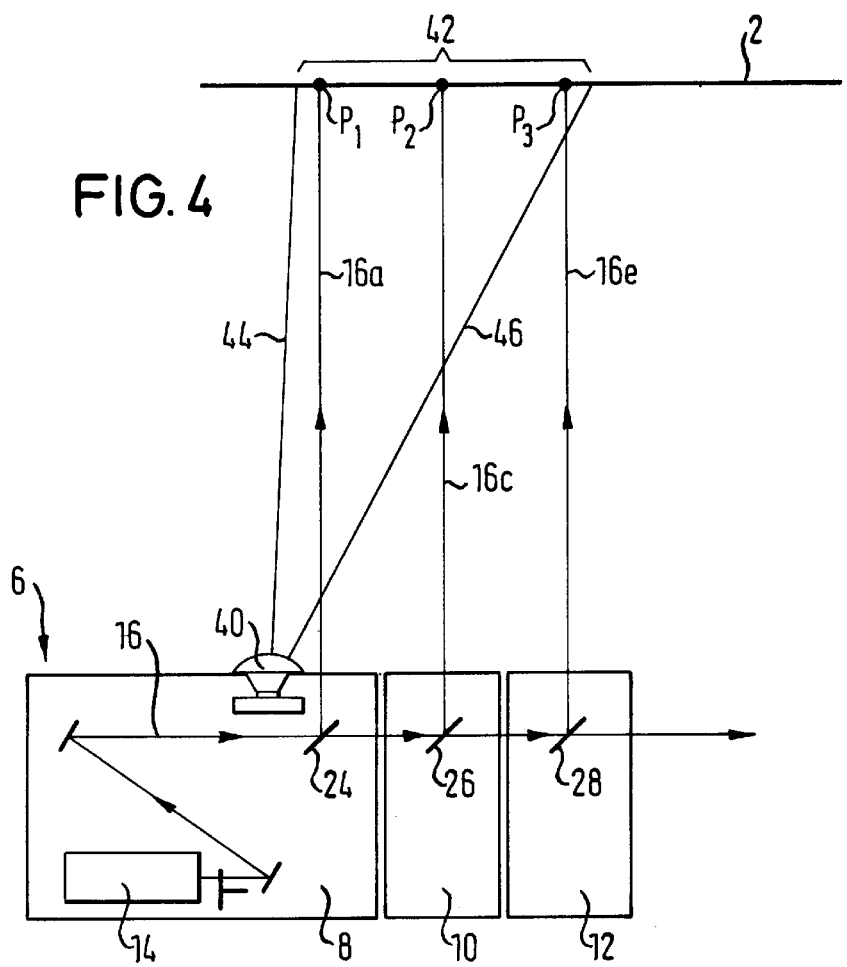
FIG. 4 is a top plan view of the embodiment illustrated in FIG. 3, including additional schematic presentations of aggregates not shown in FIG. 3.

FIGS. 3 and 4 illustrate a modified embodiment. The same reference numerals are used for similar members or ones having similar functions as in FIGS. 1 and 2 and the description is not repeated.

The embodiment according to FIGS. 3 and 4 differs from the previous embodiment only in respect of its detector means. Instead of having three separate detectors 30, 32, 34, the principal unit 8 is equipped with an IR sensitive linear detecting array which permits simultaneous sensing of the thermal rays emanating from the points to be measured $P_1$–$P_3$, $P_4$–$P_6$, and $P_7$–$P_9$, in a manner similar to that of an array of optical sensors applied in a video camera to cover a video image. In FIGS. 3 and 4 this detector array is marked by reference numeral 40.

As described with reference to the embodiment of FIGS. 1 and 2, the measuring unit 6 is movable in stepwise fashion in vertical direction so as to be able to handle points to be measured which are located along further lines $l_2$ and $l_3$.

Figure 5:
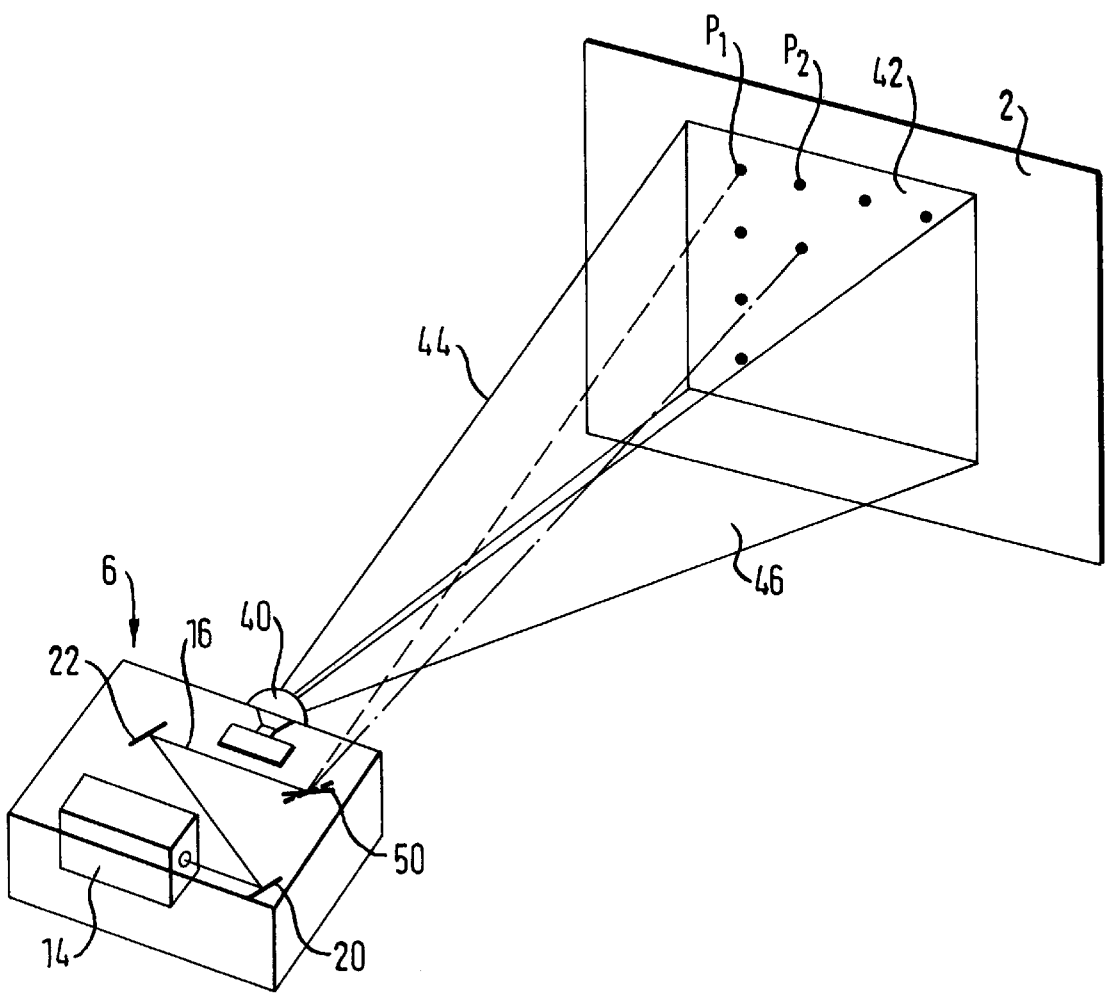
FIG. 5 is a perspective view of a third embodiment of the invention.

This is different with the embodiment shown in FIG. 5. Here, the measuring unit, again designated 6, remains fixed with respect to the workpiece during the measuring procedure. In other words, when the workpiece 2 is being moved, the measuring unit 6 is moved along with the workpiece at the same speed. The laser 14 and the deflecting mirrors 20, 22 are of the same structure and arranged in the same way as in the embodiment illustrated in FIGS. 3 and 4. The detector array of this embodiment is designed as a two-dimensional matrix. The assembly of a plurality of partly reflecting mirrors, however, is replaced by a single mirror 50 which is adapted to be pivoted and tilted about two axes. This mirror 50, not being partly reflecting and, therefore, always reflecting the full exciting beam, is controlled so as to be pivoted and tilted at the required timing (irradiation between 1 and 5 seconds duration is needed for one point to be measured). That is accomplished, for example, by a scanning system (not shown) which controls the pivoting and tilting motions of the mirror in response to the workpiece geometry.

A standard image detecting system and an image analyzing system may be used to evaluate the signals supplied by the infrared image sensor.

All three embodiments described above may be devised for additional controlled movement of the measuring unit 6 transversely of the workpiece surface so as to permit measurements to be taken also at convex or concave portions of the workpiece surface, if need be.

In an advantageous embodiment of the invention the laser is a water-cooled $CO_2$ laser. In actual practice, the workpiece 2 is moved at a speed of from 0 to 10 m/min. in the direction of arrow A. When the measuring range (based upon the baked layer thickness) is from 50 to 150 $\mu$m, the measuring accuracy is approximately ±3% of the film thickness. The actual dimension of the spot being measured at each point to be measured lies in the order of magnitude of 100 mm$^2$, at a working distance between the measuring unit 6 and the workpiece 2 of from 500 to 800 mm. The detector may be made in per se known manner of indium antimonide and be cooled with liquid nitrogen which, when in use, is consumed every twelve hours and thus needs replenishing at this interval.

What is claimed is:

1. An apparatus for photothermally examining workpiece surfaces, comprising a measuring unit including an exciting beam generator of electromagnetic radiation adapted to direct exciting beams to selected points to be measured on a workpiece surface, and further including detector means adapted to detect heat radiation emitted from the points to be measured and to forward the same to be analyzed, and comprising optical means for splitting the exciting beam into a plurality of partial beams and for directing said partial beams of the exciting beam substantially simultaneously to a plurality of points to be measured arranged in a line on the workpiece surface, wherein the measuring unit is adapted to be moved stepwise with respect to the workpiece surface in a direction parallel to the workpiece but not parallel to the line of points to be measured for directing the partial beams to different lines of the points to be measured on the workpiece surface after elapse of the measurement period.

2. The apparatus as claimed in claim 1, wherein the optical means (24, 26, 28; 50) and the multiple detecting device (30, 32, 34; 40) are integrated in the measuring unit (6).

3. The apparatus as claimed in claim 1, wherein the optical means comprises a plurality of partly reflecting mirrors (24, 26, 28) arranged one behind the other in the beam path of the exciting beam and corresponding in number to the number of points to be measured which are located along a respective one of several parallel lines ($1_1$, $1_2$, $1_3$), said mirrors reflecting a partial beam (16a, 16c, 16e) of the exciting beam (16) to the corresponding point to be measured ($P_1$–$P_9$) and transmitting the remaining partial beam (16b, 16d, 16f) to the next respective partly reflecting mirror.

4. The apparatus as claimed in claim 3, wherein the relationship between the reflected and the transmitted beam portions is so selected that the beam portion reflected on to a respective point to be measured is of the same magnitude for all the partly reflecting mirrors.

5. The apparatus as claimed in claim 3, wherein the multiple detecting device comprises a plurality of detectors (30, 32, 34) each of which is coordinated with a partly reflecting mirror (24, 26, 28).

6. The apparatus as claimed in claim 1, wherein the multiple detecting device is a heat sensitive linear or matrix detecting array (40).

7. The apparatus as claimed in claim 1, wherein the measuring unit (6) is movable with respect to the workpiece surface (2) and in synchronism with the same, the workpiece surface moving in a certain direction.

8. The apparatus as claimed in claim 1, wherein the workpiece (2) and the measuring unit (6) are movable together continuously at the same speed and parallel to each other during measurement.

9. The apparatus as claimed in claim 1, wherein the points to be measured ($P_1$–$P_3$) are arranged in a grid on the workpiece surface.

10. The apparatus as claimed in claim 1, wherein the optical means is formed by a mirror (50) adapted to be pivoted and tilted about two axes, and wherein the measuring unit (6) is not movable with respect to the workpiece (2) during measurement.

11. The apparatus as claimed in claim 10, wherein the pivoting and tilting movements of the mirror (50) are controllable, especially automatically and in adaptation to the workpiece geometry.

12. The apparatus as claimed in claim 1, wherein the analyses is carried out by means of standard image detecting and image analyzing systems.

13. Apparatus as defined in claim 1 in which the surface of the workpiece includes a powder coating not baked or annealed.

14. The apparatus as claimed in claim 1, wherein the detector means includes multiple detecting devices, each disposed to sense the heat emitted by the respective irradiated points to be measured on the workpiece surface.

15. A method of photothermally examining a moving workpiece, comprising the steps of:

splitting an electromagnetic exciting beam into a plurality of partial beams which are directed substantially simultaneously to a plurality of points to be measured arranged in a line on the moving workpiece surface to heat the workpiece surface, the plurality of partial beams of the exciting beam directed to the plurality of points to be measured in such a way that during a measurement period the partial beams move in the same direction and with the same speed as the workpiece surface to direct the partial beams to the respective plurality of points arranged in a line to be measured during said measurement period, the plurality of partial beams being move stepwise relative to the workpiece surface in a direction parallel to the workpiece surface but not parallel to the line of points to be measured for directing the partial beams to different lines of points to be measured on the workpiece surface upon expiration of the measurement period; and detecting and analyzing the heat radiation emitted from the points to be measured.

16. The method as claimed in claim 15, wherein the heat radiation emitted from the points to be measured is detected by corresponding detector elements associated with each partial beam.

17. The method as defined in claim 15 in which the surface of the workpiece includes a powder coating not baked or annealed.

* * * * *